US00PP16914P2

(12) United States Plant Patent
Mehring-Lemper

(10) Patent No.: US PP16,914 P2
(45) Date of Patent: Aug. 1, 2006

(54) ***OSTEOSPERMUM* PLANT NAMED 'WC 32/44'**

(50) Latin Name: *Osteospermum ecklonis*
Varietal Denomination: WC 32/44

(75) Inventor: Manfred Mehring-Lemper, Muenden (DE)

(73) Assignee: Ernst Benary Samenzneht GmbH, Hann-Mueden (DE)

( * ) Notice: Subject to any disclaimer, the term of this patent is extended or adjusted under 35 U.S.C. 154(b) by 0 days.

(21) Appl. No.: 11/097,693

(22) Filed: Mar. 31, 2005

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Osteospermum* plant named 'WC 32/44', characterized by its compact, upright and mounded plant habit; freely branching habit; freely and continuous flowering habit; and large inflorescences with white-colored ray florets.

1 Drawing Sheet

Botanical designation: *Osteospermum ecklonis.*
Botanical denomination: 'WC 32/44'.

BACKGROUND OF THE INVENTION

The present Invention relates to a new and distinct cultivar of *Osteospermum* plant, botanically known as *Osteospermum ecklonis*, and hereinafter referred to by the name 'WC 32/44'.

The new *Osteospermum* is a product of a planned breeding program conducted by the Inventor in Hann. Muenden, Germany. The objective of the breeding program was to create new compact and continuous flowering *Osteospermum* cultivars with large and attractive inflorescences.

The new *Osteospermum* originated from an open-pollination in 1998 of a group of unnamed proprietary *Osteospermum ecklonis* selections with white-colored flowers, not patented. The new *Osteospermum* was discovered and selected by the Inventor as a single flowering plant within the progeny of the stated open-pollination grown in a controlled environment in Hann. Muenden, Germany in 1999.

Asexual reproduction of the new *Osteospermum* by terminal vegetative cuttings was first conducted in Hann. Muenden, Germany in 1999. Asexual reproduction by cuttings has shown that the unique features of this new *Osteospermum* are stable and reproduced true to type in successive generations.

SUMMARY OF THE INVENTION

The cultivar WC 32/44 has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'WC 32/44'. These characteristics in combination distinguish 'WC 32/44' as a new and distinct *Osteospermum:*

1. Compact, upright and mounded plant habit.
2. Freely branching habit.

3. Freely and continuous flowering habit.
4. Large inflorescences with white-colored ray florets.

Plants of the new *Osteospermum* differ primarily from plants of the parent selections in plant habit and size, inflorescence size and continuity of flowering.

Plants of the new *Osteospermum* can be compared to plants of the cultivar Cape Daisy Zimba, disclosed in U.S. Plant Pat. No. 10,336. However, plants of the new *Osteospermum* are more compact, inflorescences open earlier in the morning and stay open longer at night, and have whiter ray florets than plants of the cultivar Cape Daisy Zimba.

Plants of the new *Osteospermum* can also be compared to plants of the cultivar SunSation Yellow Spot, not patented. However, plants of the new *Osteospermum* have larger inflorescences and whiter ray florets than plants of the cultivar SunSation Yellow Spot.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph at the top of the sheet is a close-up view of typical inflorescences of 'WC 32/44'.

The photograph at the bottom of the sheet comprises a side perspective view of a typical flowering plant of 'WC 32/44' grown in a container.

DETAILED BOTANICAL DESCRIPTION

The aforementioned photographs and following observations and measurements describe plants grown in Bonsall, Calif., in a polycarbonate-covered greenhouse during the winter and early spring and under conditions typical of commercial *Osteospermum* production. During the production of the plants day temperatures ranged from 21 to 24° C. and night temperatures ranged from 16 to 18° C. Plants were pinched one time. Plants had been growing for about 22 weeks in 16.5-cm containers when the photographs and the description were taken. Color references are made to The Royal Horticultural Society Colour Chart, 1995 edition, except where general terms of ordinary dictionary significance are used.

Botanical classification: *Osteospermum ecklonis* cultivar WC 32/44.

Parentage: Open-pollination of a group of unnamed proprietary *Osteospermum ecklonis* selections with white-colored flowers, not patented.

Propagation:

*Type*.—Terminal vegetative cuttings.

*Time to initiate rooting*.—About two weeks at 20° C.

*Time to produce a rooted young plant*.—About four weeks at 20° C.

*Root description*.—Fine, fibrous and well-branched.

Plant description:

*Plant form and growth habit*.—Perennial herbaceous container and garden plant. Compact, upright and mounded plant habit; inverted triangle. Freely branching habit, about six primary lateral branches each with several secondary lateral branches. Moderately vigorous growth habit.

*Plant height*.—About 38 cm.

*Plant width or area of spread*.—About 39 cm.

*Lateral branches*.—Length: About 30 cm. Diameter: About 5 mm. Internode length: About 8 mm. Aspect: Mostly upright. Strength: Strong. Texture: Smooth, glabrous. Color: 145B.

*Foliage description*.—Arrangement: Alternate; simple. Length: About 7.8 cm. Width: About 3.8 cm. Shape: Oblanceolate with prominent lobing. Apex: Acute. Base: Attenuate. Margin: Entire with random pointed lobes. Venation pattern: Pinnate. Texture, upper and lower surfaces: Sparsely pubescent; coarse. Color: Developing foliage, upper and lower surfaces: 147A. Fully expanded foliage, upper surface: 147A. Fully expanded foliage, lower surface: Darker than 147B. Venation, upper surface: 146D. Venation, lower surface: 147D. Petiole: Length: About 7 mm. Diameter: About 5 mm. Texture, upper and lower surfaces: Glabrous. Color, upper and lower surfaces: 147D.

Inflorescence description:

*Appearance*.—Solitary terminal and axillary inflorescences held above and beyond the foliage on strong peduncles. Composite inflorescence form, radially symmetrical, with ligulate-shaped ray florets and disc florets massed at the center; ray and disc florets develop acropetally on a capitulum. Inflorescences persistent. Inflorescences face mostly upright.

*Flowering response*.—Plants flower continuous and freely from the spring through the fall.

*Postproduction longevity*.—Inflorescences maintain good color and substance for about three to four days on the plant.

*Quantity of inflorescences*.—Freely flowering; at one time, about seven open inflorescences and inflorescence buds per lateral stem.

*Fragrance*.—None detected.

*Inflorescence bud*.—Length: About 1.8 cm. Diameter: About 1.1 cm. Shape: Ovoid. Color: 150C.

*Inflorescence size*.—Diameter: Large, about 8 cm. Depth (height): About 2 cm. Disc diameter: About 1.2 cm. Receptacle height: About 1 cm. Receptacle diameter: About 2.4 cm.

*Ray florets*.—Length: About 3.3 cm. Width: About 6 mm. Shape: Ligulate. Apex: Slightly emarginate. Base: Attenuate. Margin: Entire. Texture, upper and lower surfaces: Smooth, glabrous; satiny. Orientation: Initially upright then 75 to 90° from vertical. Number of ray florets per inflorescence: About 26 in one or two whorls. Color: When opening, upper surface: 155D. When opening, lower surface: 150D. Fully opened, upper surface: 155D. Fully opened, lower surface: Ground color, 155D, tinged with 150D.

*Disc florets*.—Shape: Tubular, elongated. Apex: Five-pointed. Length: About 8 mm. Width: At apex: About 2 mm. At base: Less than 1 mm. Number of disc florets per inflorescence: About 100. Color: Immature: 156C. Mature: 155D.

*Phyllaries*.—Length: About 1.2 cm. Diameter: About 1 mm. Shape: Lanceolate. Apex: Acuminate. Base: Truncate. Margin: Entire. Texture, upper and lower surfaces: Slightly coarse. Number per inflorescence: About 22 in a single whorl. Color, upper surface: 144B. Color, lower surface: 144A.

*Peduncles*.—Length, terminal peduncle: About 8.4 cm. Length, second peduncle: About 12.2 cm. Length, third peduncle: About 2.5 cm. Diameter: About 2 mm. Angle: Terminal peduncles, erect; secondary and tertiary peduncles, about 35 to 40° from vertical. Strength: Strong. Texture: Sparsely pubescent; coarse. Color: 144B.

*Reproductive organs*.—Androecium: Present on disc florets only. Stamen number: Five per floret; fused around style. Anther shape: Oblong. Anther length: About 2 mm. Anther color: 9C. Pollen amount: Scarce. Pollen color: 9A. Gynoecium: Present on both ray and disc florets. Pistil number: One per floret. Pistil length: About 6 mm. Stigma shape: Two-parted. Stigma color: 9C. Style length: About 3 mm. Style color: 155D. Ovary color: 145D.

*Seed/fruit*.—Seed and/or fruit production has not been observed.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from 4 to 35° C.

It is claimed:

1. A new and distinct cultivar of *Osteospermum* plant named 'WC 32/44', as illustrated and described.

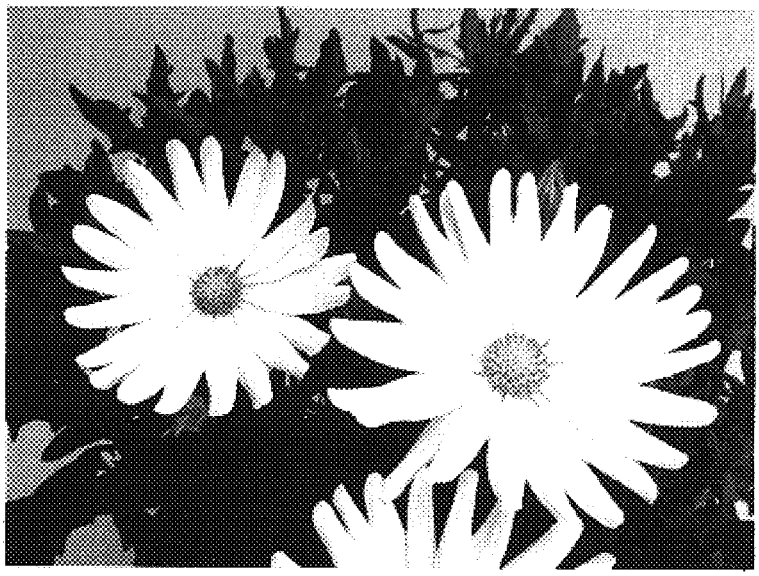
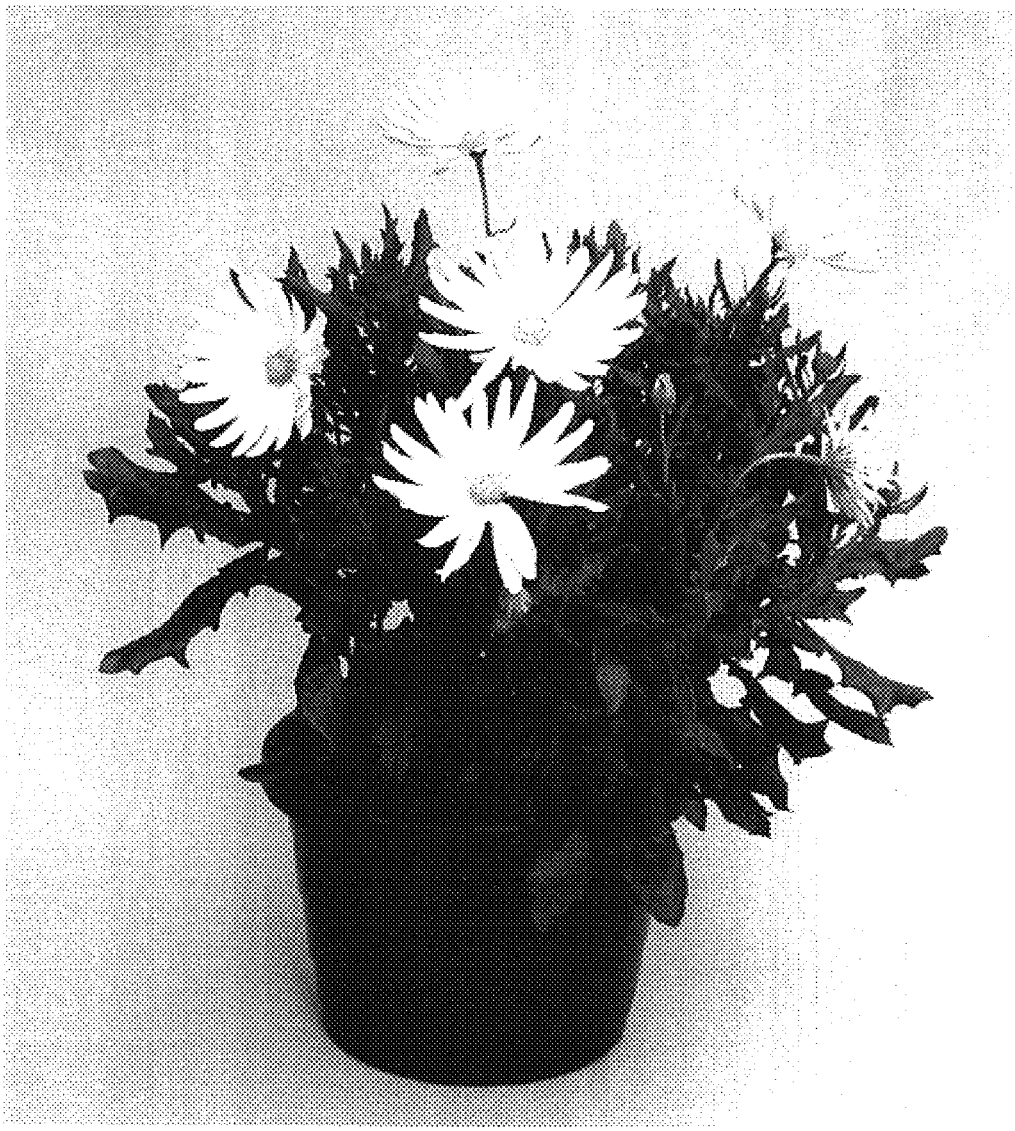

* * * * *